(12) United States Patent
Diergaarde et al.

(10) Patent No.: US 10,093,944 B2
(45) Date of Patent: Oct. 9, 2018

(54) **POWDERY MILDEW RESISTANCE PROVIDING GENES IN *CUCUMIS MELO***

(71) Applicants: Enza Zaden Beheer B.V., Enkhuizen (NL); Keygene N.V., Wageningen (NL)

(72) Inventors: Paul Johan Diergaarde, Amersfoort (NL); Leonora Johanna Gertruda van Enckevort, Wageningen (NL); Karin Ingeborg Posthuma, Enkhuizen (NL); Marinus Willem Prins, Amersfoort (NL)

(73) Assignees: Enza Zaden Beheer B.V., Enkhuizen (NL); Keygene N.V., Wageningen (NL)

( * ) Notice: Subject to any disclaimer, the term of this patent is extended or adjusted under 35 U.S.C. 154(b) by 0 days.

(21) Appl. No.: 15/610,755

(22) Filed: Jun. 1, 2017

(65) Prior Publication Data

US 2017/0275646 A1    Sep. 28, 2017

Related U.S. Application Data

(62) Division of application No. 14/002,259, filed as application No. PCT/EP2012/053208 on Feb. 24, 2012, now Pat. No. 9,688,998.

(30) Foreign Application Priority Data

Mar. 1, 2011    (WO) ................. PCT/EP2011/053053

(51) Int. Cl.
*C12N 15/82*     (2006.01)
*C07K 14/415*    (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS 6,576,814 B1    6/2003    Briggs et al.

FOREIGN PATENT DOCUMENTS

| EP | 1719410 A1 | 11/2006 |
|---|---|---|
| JP | 2006304684 A | 11/2006 |
| WO | 9804586 A2 | 2/1998 |
| WO | 9947552 A2 | 9/1999 |
| WO | WO9947552 A2 * | 9/1999 ........... C07K 14/415 |
| WO | 2008017706 A1 | 2/2008 |

OTHER PUBLICATIONS

Bai et al., "Naturally Occurring Broad-Spectrum Powdery Mildew Resistance in a Central American Tomato Accession is Caused by Loss of Mlo Function", Molecular Plant-Microbe Interactions, 2008, p. 30-30, vol. 21, No. 1.
Cheng et al., "Molecular cloning and expression analysis of CmMlo1 in melon", Mol Biol Rep, 2012, p. 1903-1907, vol. 39.
Dry, "Vitis vinifera MLO-like protein 17 (ML017) mRNA, complete cds.", Jul. 1, 2009, one (1) page, XP002674309, retrieved from EBI accession No. EM_PL:EU812238, Database accession No. EU812238 sequence.
Gonzalez-Ibas et al., "MELOGEN: an EST database for melon functional genomics", BMC Genomics, 2007, seventeen (17) pages, vol. 8.
Ibeas et al., "*Cucumis melo* subsp. melo EST, clone CI_25-C11-M13R", Sep. 25, 2007, one (1) page, XP002674262, retrieved from EBI accession No. EMBL: AM735244, Database accession No. AM735244 sequence.
Jorgensen, "discovery, characterization and exploitation of Mlo powdery mildew resistance in barley", Euphytica, 1992, p. 141-152, vol. 63.
Kuzuya et al., "Powdery mildew (Podosphaera xanthii) resistance in melon is categorized into two types based on inhibition of the infection processes", J. Exp. Botany, 2006, p. 2093-2100, vol. 57, No. 9.
Panstruga, "Serpentine plant MLO proteins as entry portals for powdery mildew fungi", Biochemical Society, Apr. 2005, p. 389-392, vol. 33.
Schweizer et al., "Double-stranded RNA interferes with gene function at the single-cell level in cereals", The Plant Journal, 2000, p. 895-903, vol. 24, No. 6.

\* cited by examiner

*Primary Examiner* — Brent T Page
(74) *Attorney, Agent, or Firm* — The Webb Law Firm

(57) ABSTRACT

The present invention relates to powdery mildew resistance providing genes of the *Cucumis* family, and especially *Cucumis melo*, wherein said resistance is provided by impairment of the present genes. Further, the present invention relates plants comprising the present impaired resistance conferring genes and seeds, embryos or other propagation material thereof. Especially, the present invention relates to powdery mildew resistance conferring genes, wherein the amino acid sequence encoded by said resistance conferring gene is selected from the group consisting of SEQ ID No. 2, SEQ ID No. 4, SEQ ID No. 6, SEQ ID. No. 8, SEQ ID No. 10, SEQ ID No. 12 and SEQ ID No. 14, and amino acid sequences with more than 70% identity, preferably more than 80% identity, more preferably more than 90% identity, and most preferably more than 95% identity.

7 Claims, 3 Drawing Sheets
Specification includes a Sequence Listing.

SEQUENCE LISTING

<160> NUMBER OF SEQ ID NOS: 24

<210> SEQ ID NO 1
<211> LENGTH: 1713
<212> TYPE: DNA
<213> ORGANISM: Cucumis melo

<400> SEQUENCE: 1

```
atggctgaat gtggaacaga gcagcgtact ttggaagata cttcaacttg ggctgttgcg      60
gttgtttgtt ttttcttggt tgttatttca atcttcattg aacatgtcat tcacctcact     120
ggaaagtggc tggagaaaaa gcacaagcca gctcttgttg aagctctaga aaaggttaaa     180
gcagagctta tgctattggg atttatatcc ctacttctaa cggtaggcca agatgctgtc     240
actcaaattt gtgtttcgaa ggagcttgca gcaacttggc ttccctgtgc agcaagagct     300
aaagcaggag taaaagttgc gaagaacagt cgtcttagac ttcttgaatt tttagatcct     360
gactatggtt cgaggcgtat tttagcctcg aaaggagatg atgcatgcgc taagaggggc     420
```

```
caactcgctt tcgtgtcggc atatggaatc catcagctcc atattttcat cttcgtcttg    480
gctgtcttcc atgtcctata ttgcatcatc actttggctt tcggcagaac aaagatgagc    540
aaatggaagg cctgggagga tgaaaccaag acaattgaat accagtacta taatgatcca    600
gcaagattta gatttgccag agatactacg tttggacgcc gacacttgag cttctggagt    660
cgtacaccaa tttccctctg gattgtttgt ttcttcagac aattctttgg atcagttacc    720
aaggttgatt acatgacact gagacatgga ttcattgttg cacatctagc acccggaagt    780
gaagtaaaat ttgatttcca caaatacatt agcagatctc tggaagacga ctttaaagtt    840
gttgtgggga ttagtcccgc aatgtggcta tttgctgttc tcttcatcct aactaataca    900
aatgggtggt attcatatct atggctgcct ttcatttcct tatttataat tctattggtg    960
ggaacaaagc tccatgtcat tataactcat atgggattga caattcaaga aaggggtcat   1020
gttgtgaagg gtgttccggt cgttcagcct cgggatgacc tgttttggtt tggccgtcca   1080
caacttattc tcttcctgat ccactttgtt ctctttatga atgcatttca gcttgccttc   1140
tttgcttgga ccacatatgc attcacgtgg aggggttgtt tccatcagcg aattgaagat   1200
attgccatca gactctcaat ggggttatc atacaagttc tctgcagtta tgtcacactc   1260
ccactctatg ctttggttac tcagatgggc tctaacatga accaaccat tttcaacgac   1320
cgagtggcga cggcattgaa gaactggcac cactccgcca agaagaacat gaagcagcat   1380
cgcaacccag acagtacctc accattctca agcaggccaa caactccaac tcacggcatg   1440
tctcctattc accttctgca caaacatcag catggcagca catctcccag gctatccgat   1500
gccgaacccg atcggtggga agagttacct ccttcttcac accataatag agcccatgat   1560
aatcaagatc aacaagaaca atctgagact agtagagaac aggagatgac ggttcaacga   1620
ccaagttcaa gtgaaaccgg ttccataaca cgtcctgctc gccctcatca ggaaatcact   1680
aggagtccat cggacttctc atttgccaaa tga                                1713

<210> SEQ ID NO 2
<211> LENGTH: 570
<212> TYPE: PRT
<213> ORGANISM: Cucumis melo

<400> SEQUENCE: 2

Met Ala Glu Cys Gly Thr Glu Gln Arg Thr Leu Glu Asp Thr Ser Thr
1               5                   10                  15

Trp Ala Val Ala Val Val Cys Phe Phe Leu Val Val Ile Ser Ile Phe
            20                  25                  30

Ile Glu His Val Ile His Leu Thr Gly Lys Trp Leu Glu Lys Lys His
        35                  40                  45

Lys Pro Ala Leu Val Glu Ala Leu Glu Lys Val Lys Ala Glu Leu Met
    50                  55                  60

Leu Leu Gly Phe Ile Ser Leu Leu Leu Thr Val Gly Gln Asp Ala Val
65                  70                  75                  80

Thr Gln Ile Cys Val Ser Lys Glu Leu Ala Ala Thr Trp Leu Pro Cys
                85                  90                  95

Ala Ala Arg Ala Lys Ala Gly Val Lys Val Ala Lys Asn Ser Arg Leu
            100                 105                 110

Arg Leu Leu Glu Phe Leu Asp Pro Asp Tyr Gly Ser Arg Arg Ile Leu
        115                 120                 125

Ala Ser Lys Gly Asp Asp Ala Cys Ala Lys Arg Gly Gln Leu Ala Phe
    130                 135                 140
```

```
Val Ser Ala Tyr Gly Ile His Gln Leu His Ile Phe Ile Val Leu
145                 150                 155                 160

Ala Val Phe His Val Leu Tyr Cys Ile Ile Thr Leu Ala Phe Gly Arg
                165                 170                 175

Thr Lys Met Ser Lys Trp Lys Ala Trp Glu Asp Glu Thr Lys Thr Ile
            180                 185                 190

Glu Tyr Gln Tyr Tyr Asn Asp Pro Ala Arg Phe Arg Phe Ala Arg Asp
        195                 200                 205

Thr Thr Phe Gly Arg Arg His Leu Ser Phe Trp Ser Arg Thr Pro Ile
    210                 215                 220

Ser Leu Trp Ile Val Cys Phe Phe Arg Gln Phe Phe Gly Ser Val Thr
225                 230                 235                 240

Lys Val Asp Tyr Met Thr Leu Arg His Gly Phe Ile Val Ala His Leu
                245                 250                 255

Ala Pro Gly Ser Glu Val Lys Phe Asp Phe His Lys Tyr Ile Ser Arg
            260                 265                 270

Ser Leu Glu Asp Asp Phe Lys Val Val Gly Ile Ser Pro Ala Met
        275                 280                 285

Trp Leu Phe Ala Val Leu Phe Ile Leu Thr Asn Thr Asn Gly Trp Tyr
    290                 295                 300

Ser Tyr Leu Trp Leu Pro Phe Ile Ser Leu Phe Ile Ile Leu Leu Val
305                 310                 315                 320

Gly Thr Lys Leu His Val Ile Ile Thr His Met Gly Leu Thr Ile Gln
                325                 330                 335

Glu Arg Gly His Val Val Lys Gly Val Pro Val Val Gln Pro Arg Asp
            340                 345                 350

Asp Leu Phe Trp Phe Gly Arg Pro Gln Leu Ile Leu Phe Leu Ile His
        355                 360                 365

Phe Val Leu Phe Met Asn Ala Phe Gln Leu Ala Phe Phe Ala Trp Thr
    370                 375                 380

Thr Tyr Ala Phe Thr Trp Arg Gly Cys Phe His Gln Arg Ile Glu Asp
385                 390                 395                 400

Ile Ala Ile Arg Leu Ser Met Gly Val Ile Gln Val Leu Cys Ser
                405                 410                 415

Tyr Val Thr Leu Pro Leu Tyr Ala Leu Val Thr Gln Met Gly Ser Asn
            420                 425                 430

Met Arg Pro Thr Ile Phe Asn Asp Arg Val Ala Thr Ala Leu Lys Asn
        435                 440                 445

Trp His His Ser Ala Lys Lys Asn Met Lys Gln His Arg Asn Pro Asp
    450                 455                 460

Ser Thr Ser Pro Phe Ser Ser Arg Pro Thr Thr Pro Thr His Gly Met
465                 470                 475                 480

Ser Pro Ile His Leu Leu His Lys His Gln His Gly Ser Thr Ser Pro
                485                 490                 495

Arg Leu Ser Asp Ala Glu Pro Arg Trp Glu Glu Leu Pro Pro Ser
            500                 505                 510

Ser His His Asn Arg Ala His Asp Asn Gln Asp Gln Glu Gln Ser
        515                 520                 525

Glu Thr Ser Arg Glu Gln Glu Met Thr Val Gln Arg Pro Ser Ser Ser
    530                 535                 540

Glu Thr Gly Ser Ile Thr Arg Pro Ala Arg Pro His Gln Glu Ile Thr
545                 550                 555                 560

Arg Ser Pro Ser Asp Phe Ser Phe Ala Lys
```

<210> SEQ ID NO 3
<211> LENGTH: 1704
<212> TYPE: DNA
<213> ORGANISM: Cucumis melo

<400> SEQUENCE: 3

```
atgtttctgg ttgtttatta tttgtgtttg agtttgttgt gggggaaatc gtggggagct      60
ccggccagcg atggcaccac gagggagctc gatcagactc cgacgtgggc tgttgctggt     120
gtttgtgcta ttatcatcct tatttctatc gccttggaga aactccttca taaagctgga     180
acgtggctca cggaaaagca aagagagct ctctttgaag ctctggagaa agttaaagct      240
gagctgatga ttctgggttt catttctcta ctcctcacct ttggacagaa ctacatcatt     300
aaaatctgca ttcccacgaa ggttgcaaat actatgttgc catgtgctgc caagaggac     360
aaattggaga aggcagatga gggcgaacat catcgacgac tactaatgta tgaacggagg     420
ttcctggctg ctgctggtgg cgctgttagt tgcaaagaag gtcatgtgcc gcttatatct     480
atctcgggat tgcatcagtt gcacttgttt atcttcttct tagccgtatt tcatgtggta     540
tatagtgcca tcaaatgat gcttggggagg ctaaagattc gaggttggaa ggcatgggag     600
gaggagacct caactcacaa ttacgagttc tcaaatgata tgcacgatt caggcttact     660
cacgaaacat catttgtgaa agcccacacg agttttttgga caaaacttcc tgtcttcttt     720
tatattggat gcttcttccg acaattttc aagtccgttg gtaaggctga ctacctggca     780
ttacgaaatg gattcatcgc tgttcacctt gctccaggaa gtaaatttga ctttcaaaaa     840
tatatcaaaa ggtctctaga agatgacttc aaaataattg tgggagtgag tcccgtgctt     900
tggacatcgt ttgtggtctt cttgctcata aatgttacg gatggcaagc attgttttgg     960
acatccttag tccctgtgat cataatcctg gctgttggaa caaagcttca aggaattatg    1020
acaaagatgg ctcttgaaat tacagaaaga catgctgttg tccaaggaat tcctctcgtt    1080
caggcatcag ataaatattt ttggtttggc aagcctcagc tggttcttta cctcatccac    1140
ttcgctttat tttcgaatgc attccaaata acatacttct tctggatttg gtattccttt    1200
gggttaaaat cctgcttcca tactgatttc aagcttgcaa tcattaaagt tggtttcggg    1260
gttggcgttc tctgtctctg cagttatata actcttccac tctatgctct tgtcactcag    1320
gtgggtactc gtatgaagaa gtcgatcttt gacgaacaaa catcgaaggc tcttaagaaa    1380
tggcacatgg ctgttaagaa gcgacatggg aagtccccga ctcgaaaact agggagtcca    1440
agtgcgtcac caattcatcc atcagcagga tacacattgc atcgtttcaa gacgacaggt    1500
cactcaaaca gatcatccat gtatgatgag aatgatgcat cagattatga agttgatcca    1560
ttgtcgccta aagtcgatac tccaaatttt acggttagaa tagaccgtgc tgatgaacat    1620
catgttgaaa taattgaacc ccagcataca gagaaaagga atgaagacga tttctctttt    1680
gtcaaacctg gaccaacaaa atga                                           1704
```

<210> SEQ ID NO 4
<211> LENGTH: 567
<212> TYPE: PRT
<213> ORGANISM: Cucumis melo

<400> SEQUENCE: 4

```
Met Phe Leu Val Val Tyr Tyr Leu Cys Leu Ser Leu Leu Trp Gly Lys
1               5                   10                  15
```

```
Ser Trp Gly Ala Pro Ala Ser Asp Gly Thr Thr Arg Glu Leu Asp Gln
            20                  25                  30

Thr Pro Thr Trp Ala Val Ala Gly Val Cys Ala Ile Ile Ile Leu Ile
            35                  40                  45

Ser Ile Ala Leu Glu Lys Leu Leu His Lys Ala Gly Thr Trp Leu Thr
 50                  55                  60

Glu Lys His Lys Arg Ala Leu Phe Glu Ala Leu Glu Lys Val Lys Ala
 65                  70                  75                  80

Glu Leu Met Ile Leu Gly Phe Ile Ser Leu Leu Thr Phe Gly Gln
                85                  90                  95

Asn Tyr Ile Ile Lys Ile Cys Ile Pro Thr Lys Val Ala Asn Thr Met
                100                 105                 110

Leu Pro Cys Ala Ala Lys Glu Asp Lys Leu Glu Lys Ala Asp Glu Gly
            115                 120                 125

Glu His His Arg Arg Leu Leu Met Tyr Glu Arg Arg Phe Leu Ala Ala
            130                 135                 140

Ala Gly Gly Ala Val Ser Cys Lys Glu Gly His Val Pro Leu Ile Ser
145                 150                 155                 160

Ile Ser Gly Leu His Gln Leu His Leu Phe Ile Phe Phe Leu Ala Val
                165                 170                 175

Phe His Val Val Tyr Ser Ala Ile Thr Met Met Leu Gly Arg Leu Lys
                180                 185                 190

Ile Arg Gly Trp Lys Ala Trp Glu Glu Thr Ser Thr His Asn Tyr
                195                 200                 205

Glu Phe Ser Asn Asp Asn Ala Arg Phe Arg Leu Thr His Glu Thr Ser
210                 215                 220

Phe Val Lys Ala His Thr Ser Phe Trp Thr Lys Leu Pro Val Phe Phe
225                 230                 235                 240

Tyr Ile Gly Cys Phe Phe Arg Gln Phe Phe Lys Ser Val Gly Lys Ala
                245                 250                 255

Asp Tyr Leu Ala Leu Arg Asn Gly Phe Ile Ala Val His Leu Ala Pro
            260                 265                 270

Gly Ser Lys Phe Asp Phe Gln Lys Tyr Ile Lys Arg Ser Leu Glu Asp
            275                 280                 285

Asp Phe Lys Ile Ile Val Gly Val Ser Pro Val Leu Trp Thr Ser Phe
290                 295                 300

Val Val Phe Leu Leu Ile Asn Val Tyr Gly Trp Gln Ala Leu Phe Trp
305                 310                 315                 320

Thr Ser Leu Val Pro Val Ile Ile Leu Ala Val Gly Thr Lys Leu
                325                 330                 335

Gln Gly Ile Met Thr Lys Met Ala Leu Glu Ile Thr Glu Arg His Ala
                340                 345                 350

Val Val Gln Gly Ile Pro Leu Val Gln Ala Ser Asp Lys Tyr Phe Trp
            355                 360                 365

Phe Gly Lys Pro Gln Leu Val Leu Tyr Leu Ile His Phe Ala Leu Phe
            370                 375                 380

Ser Asn Ala Phe Gln Ile Thr Tyr Phe Phe Trp Ile Trp Tyr Ser Phe
385                 390                 395                 400

Gly Leu Lys Ser Cys Phe His Thr Asp Phe Lys Leu Ala Ile Ile Lys
                405                 410                 415

Val Gly Phe Gly Val Gly Val Leu Cys Leu Cys Ser Tyr Ile Thr Leu
            420                 425                 430

Pro Leu Tyr Ala Leu Val Thr Gln Val Gly Thr Arg Met Lys Lys Ser
```

```
        435                 440                 445
Ile Phe Asp Glu Gln Thr Ser Lys Ala Leu Lys Lys Trp His Met Ala
            450                 455                 460

Val Lys Lys Arg His Gly Lys Ser Pro Thr Arg Lys Leu Gly Ser Pro
465                 470                 475                 480

Ser Ala Ser Pro Ile His Pro Ser Ala Gly Tyr Thr Leu His Arg Phe
                485                 490                 495

Lys Thr Thr Gly His Ser Asn Arg Ser Ser Met Tyr Asp Glu Asn Asp
                500                 505                 510

Ala Ser Asp Tyr Glu Val Asp Pro Leu Ser Pro Lys Val Asp Thr Pro
            515                 520                 525

Asn Phe Thr Val Arg Ile Asp Arg Ala Asp Glu His His Val Glu Ile
            530                 535                 540

Ile Glu Pro Gln His Thr Glu Lys Arg Asn Glu Asp Asp Phe Ser Phe
545                 550                 555                 560

Val Lys Pro Gly Pro Thr Lys
                565

<210> SEQ ID NO 5
<211> LENGTH: 1779
<212> TYPE: DNA
<213> ORGANISM: Cucumis melo

<400> SEQUENCE: 5
atggccggag gtggcgccgg aaggtccttg aagagacgc cgacatgggc cgtcgccgcc      60
gtctgctttg ttttggttct gatttctatt atcatcgaac acattctcca tctcatcgga     120
aagtggctaa agaagaaaca caaacgagct ctttacgaag ctctagagaa gatcaaatca     180
gaactgatgc tgttgggatt catatcgctg ctgctgacgg tgggacaaag cctaatcaca     240
aatgtttgta taccaccaga cgtggcagcc acgtggcatc catgtagtcc tcaaagagaa     300
gaggaattaa ctaagaagc cgacctggtc gattccgacc acaatcgtcg aaacttctc      360 gcgacggtct cccatcatgt caacgccacc ttccgccgtt ccctcgcggc tgccggtggt     420
accgacaaat gtgctgccaa gggtaaagtt ccatttgtat cggaagggg tattcatcag     480 ctacatatat tcatcttcgt attggccgtt ttccatgttt tgtattgtgt tctaacttta     540
gctctgggca atgccaagat gagaagttgg aagtcatggg agaaagagac tagaacagtg     600
gagtaccaat tctcacacga tccggaacgg tttcgatttg caagagacac gtcgtttggg     660
agaagacatt taagcttttg acaaaaatcc cctttcctca tatggattgt ttgtttcttc     720
agacaattcg ttaggtcggt tccaaaggtt gattacttga ccttaagaca tggtttcgtc     780
atggcacatc tggcaccccca cagcgatcag aaatttgact ttcaaaaata cataaaacga     840
tctcttgaag aagatttcaa ggtggtggtc agcatcagcc ctccgatatg gttctttgct     900
gtcctcttcc tacttttcaa caccaacggg tggagggctt atctatggct acccctttgtt     960 ccattaatta tagtgttatt ggtggggaca aagttgcaag tgataataac gaagatggcg    1020
ctgaggatac aagaaagagg agaagtggtg aaaggagtac cggtggtaga gccggggat     1080 gacctctttt ggttcaatcg ccctcgtctt attcttacc ttatcaattt tgtcctcttc    1140
cagaatgctt ttcagcttgc cttttttgct tggacttgga aagagtttgg gatgaaatct    1200
tgtttccatg aacacaccga ggatttggtc atcagaataa cgatgggagt cctcgttcaa    1260
atcctttgca gttacgtcac attgccactc tatgctctag tcacacagat gggttcgacg    1320
atgaagccta cgattttcaa tgaaagagta gcgacggcat tgagaaattg gcaccacacg    1380
```

```
gctcgtaaac acataaaaca aaatcgcggc tcaatgacgc cgatgtcgag ccgtcctgcc   1440
accccctctc accacttgtc accggtccac cttcttcgcc actatcgaag cgaattagac   1500
agcgtccata cgtctcctag aagatccaat ttcgacaccg atcaatggga ccctgagtcc   1560
ccttcccctt cccaccgatt ccaccgtcgt cccatcctg gcgacggctc catttccaac    1620
catcaccgcg acgtggaggc cggtgatctt gatgccgatg ttgattcgcc tcaacccgat   1680
cggacgactc aatcgatgaa cccaataaat attgagcaac accaaattga cgtggggtct   1740
aatgaattct cattcgatag aagagttgat agactatga                          1779
```

<210> SEQ ID NO 6
<211> LENGTH: 592
<212> TYPE: PRT
<213> ORGANISM: Cucumis melo

<400> SEQUENCE: 6

```
Met Ala Gly Gly Gly Ala Gly Arg Ser Leu Glu Glu Thr Pro Thr Trp
  1               5                  10                  15

Ala Val Ala Ala Val Cys Phe Val Leu Val Leu Ile Ser Ile Ile Ile
             20                  25                  30

Glu His Ile Leu His Leu Ile Gly Lys Trp Leu Lys Lys His Lys
         35                  40                  45

Arg Ala Leu Tyr Glu Ala Leu Glu Lys Ile Lys Ser Glu Leu Met Leu
     50                  55                  60

Leu Gly Phe Ile Ser Leu Leu Thr Val Gly Gln Ser Leu Ile Thr
 65                  70                  75                  80

Asn Val Cys Ile Pro Pro Asp Val Ala Ala Thr Trp His Pro Cys Ser
                 85                  90                  95

Pro Gln Arg Glu Glu Leu Thr Lys Glu Ala Asp Leu Val Asp Ser
            100                 105                 110

Asp His Asn Arg Arg Lys Leu Leu Ala Thr Val Ser His His Val Asn
        115                 120                 125

Ala Thr Phe Arg Arg Ser Leu Ala Ala Ala Gly Gly Thr Asp Lys Cys
    130                 135                 140

Ala Ala Lys Gly Lys Val Pro Phe Val Ser Glu Gly Gly Ile His Gln
145                 150                 155                 160

Leu His Ile Phe Ile Phe Val Leu Ala Val Phe His Val Leu Tyr Cys
                165                 170                 175

Val Leu Thr Leu Ala Leu Gly Asn Ala Lys Met Arg Ser Trp Lys Ser
            180                 185                 190

Trp Glu Lys Glu Thr Arg Thr Val Glu Tyr Gln Phe Ser His Asp Pro
        195                 200                 205

Glu Arg Phe Arg Phe Ala Arg Asp Thr Ser Phe Gly Arg His Leu
    210                 215                 220

Ser Phe Trp Thr Lys Ser Pro Phe Leu Ile Trp Ile Val Cys Phe Phe
225                 230                 235                 240

Arg Gln Phe Val Arg Ser Val Pro Lys Val Asp Tyr Leu Thr Leu Arg
                245                 250                 255

His Gly Phe Val Met Ala His Leu Ala Pro His Ser Asp Gln Lys Phe
            260                 265                 270

Asp Phe Gln Lys Tyr Ile Lys Arg Ser Leu Glu Glu Asp Phe Lys Val
        275                 280                 285

Val Val Ser Ile Ser Pro Pro Ile Trp Phe Phe Ala Val Leu Phe Leu
    290                 295                 300
```

Leu Phe Asn Thr Asn Gly Trp Arg Ala Tyr Leu Trp Leu Pro Phe Val
305                 310                 315                 320

Pro Leu Ile Ile Val Leu Leu Val Gly Thr Lys Leu Gln Val Ile Ile
            325                 330                 335

Thr Lys Met Ala Leu Arg Ile Gln Glu Arg Gly Glu Val Lys Gly
        340                 345                 350

Val Pro Val Val Glu Pro Gly Asp Asp Leu Phe Trp Phe Asn Arg Pro
    355                 360                 365

Arg Leu Ile Leu Tyr Leu Ile Asn Phe Val Leu Phe Gln Asn Ala Phe
    370                 375                 380

Gln Leu Ala Phe Phe Ala Trp Thr Trp Lys Glu Phe Gly Met Lys Ser
385                 390                 395                 400

Cys Phe His Glu His Thr Glu Asp Leu Val Ile Arg Ile Thr Met Gly
                405                 410                 415

Val Leu Val Gln Ile Leu Cys Ser Tyr Val Thr Leu Pro Leu Tyr Ala
            420                 425                 430

Leu Val Thr Gln Met Gly Ser Thr Met Lys Pro Thr Ile Phe Asn Glu
        435                 440                 445

Arg Val Ala Thr Ala Leu Arg Asn Trp His His Thr Ala Arg Lys His
    450                 455                 460

Ile Lys Gln Asn Arg Gly Ser Met Thr Pro Met Ser Ser Arg Pro Ala
465                 470                 475                 480

Thr Pro Ser His His Leu Ser Pro Val His Leu Leu Arg His Tyr Arg
                485                 490                 495

Ser Glu Leu Asp Ser Val His Thr Ser Pro Arg Ser Asn Phe Asp
            500                 505                 510

Thr Asp Gln Trp Asp Pro Glu Ser Pro Ser Pro Ser His Arg Phe His
        515                 520                 525

Arg Arg Pro His Pro Gly Asp Gly Ser Ile Ser Asn His His Arg Asp
    530                 535                 540

Val Glu Ala Gly Asp Leu Asp Ala Asp Val Asp Ser Pro Gln Pro Asp
545                 550                 555                 560

Arg Thr Thr Gln Ser Met Asn Pro Ile Asn Ile Glu Gln His Gln Ile
                565                 570                 575

Asp Val Gly Ser Asn Glu Phe Ser Phe Asp Arg Arg Val Asp Arg Leu
            580                 585                 590

<210> SEQ ID NO 7
<211> LENGTH: 1548
<212> TYPE: DNA
<213> ORGANISM: Cucumis melo

<400> SEQUENCE: 7
atgggcggcg gaggtgaagg aacgacgctg gaattcactc cgacgtgggt tgtagccgcc      60
gtatgtaccg tcatcgttgc catttccctc gccttagagc gtcttcttca ctttctcggc     120
agatacctca aaagcaagaa tcaaaagccg ctcaatgaag ctcttcagaa agttaaagaa     180
gaattgatgc ttttgggggtt catttcactt ctgctcactg tatttcaagg caccatctct     240
aaattgtgtg ttcctgagag tttgaccgaa catttacttc cgtgtgatct gaaggataaa     300
ccgaaagctg aacatggttc gccctcaggt gaaaccggtt cgtcaacgac gaagcatttt     360
caaactttct tgtttcgag tatttctggt acggccagac ggcttcttgc tgagggatct     420
gcttcacagg ctggttattg tgccaaaaag aataaggtgc cattgctatc actcgaagca     480

-continued

```
ttgcatcatc tacatatttt tatcttcatc ctagctatcg tccacgtaac attttgcgtt    540
ctcactgtag ttttttggagg attgaagatt cgccagtgga agcattggga ggattctatt   600
gcaaaagaga attatgatac tgaacaagtt ctaaaaccaa aagtcactca tgtccatcaa    660
catgctttta tcaaagacca ctttttgggc tttggtaaag attcagctct tcttggttgg   720
ttgcattcct ttctcaagca attttatgct tctgtaacaa aatcagatta tgcaacgtta    780
cggcttggtt tcattatgac gcactgcagg ggaaatccga agtttaattt tcacaagtac    840
atgatacgtg ctcttgaaga tgacttcaag catgttgttg aatcaggag ttggtatctt     900
tggatattcg tggttgtctt cttgttcctt aatgtcagtg gttggcatac atattttgg    960
atagcattca ttcctttcgt tcttttgctt gctgtgggaa cgaagctgga acatgtgata   1020
acccagctgg ctcatgaggt tgcagagaag cacgtagcaa ttgaaggtga tttagtagtc   1080
caaccgtttg atgatcactt ttggtttcaa cgtcctcgta ttgttctctt cttgatccac   1140
ttcatacttt tccaaaatgc ttttgagatt ggatttttct tctggatatg ggttcaatat   1200
ggatttgact cgtgcatcat gggacaagtc cgctatatca ttccaaggct catcattggg   1260
gtgtttgtcc aggttctttg cagttacagc acccttccgc tctacgccat tgtcactcag   1320
atgggaagtt ctttcaagaa agcaatcttt gatgaacatg tacaagtagg ctagttggc    1380
tgggctcaga aggtgaagaa agaaaggga cttagagcag ctgctgatgg ctccagtcaa   1440
ggagtcaagg aaggtggttc aactgtgggg attcagttgg gaaatgttat gcgcaaggct   1500
tctgcacctc aagaaattaa gcctgatgac tccaaatcaa ctcattaa                1548
```

<210> SEQ ID NO 8
<211> LENGTH: 515
<212> TYPE: PRT
<213> ORGANISM: Cucumis melo

<400> SEQUENCE: 8

```
Met Gly Gly Gly Gly Glu Gly Thr Thr Leu Glu Phe Thr Pro Thr Trp
  1               5                  10                  15

Val Val Ala Ala Val Cys Thr Val Ile Val Ala Ile Ser Leu Ala Leu
             20                  25                  30

Glu Arg Leu Leu His Phe Leu Gly Arg Tyr Leu Lys Ser Lys Asn Gln
         35                  40                  45

Lys Pro Leu Asn Glu Ala Leu Gln Lys Val Lys Glu Glu Leu Met Leu
     50                  55                  60

Leu Gly Phe Ile Ser Leu Leu Thr Val Phe Gln Gly Thr Ile Ser
 65                  70                  75                  80

Lys Leu Cys Val Pro Glu Ser Leu Thr Glu His Leu Leu Pro Cys Asp
                 85                  90                  95

Leu Lys Asp Lys Pro Lys Ala Glu His Gly Ser Pro Ser Gly Glu Thr
            100                 105                 110

Gly Ser Ser Thr Thr Lys His Phe Gln Thr Phe Phe Val Ser Ser Ile
        115                 120                 125

Ser Gly Thr Ala Arg Arg Leu Leu Ala Glu Gly Ser Ala Ser Gln Ala
    130                 135                 140

Gly Tyr Cys Ala Lys Lys Asn Lys Val Pro Leu Leu Ser Leu Glu Ala
145                 150                 155                 160

Leu His His Leu His Ile Phe Ile Phe Ile Leu Ala Ile Val His Val
                165                 170                 175

Thr Phe Cys Val Leu Thr Val Val Phe Gly Gly Leu Lys Ile Arg Gln
            180                 185                 190
```

Trp Lys His Trp Glu Asp Ser Ile Ala Lys Glu Asn Tyr Asp Thr Glu
            195                 200                 205

Gln Val Leu Lys Pro Lys Val Thr His Val His Gln His Ala Phe Ile
210                 215                 220

Lys Asp His Phe Leu Gly Phe Gly Lys Asp Ser Ala Leu Leu Gly Trp
225                 230                 235                 240

Leu His Ser Phe Leu Lys Gln Phe Tyr Ala Ser Val Thr Lys Ser Asp
            245                 250                 255

Tyr Ala Thr Leu Arg Leu Gly Phe Ile Met Thr His Cys Arg Gly Asn
            260                 265                 270

Pro Lys Phe Asn Phe His Lys Tyr Met Ile Arg Ala Leu Glu Asp Asp
            275                 280                 285

Phe Lys His Val Val Gly Ile Arg Ser Trp Tyr Leu Trp Ile Phe Val
            290                 295                 300

Val Val Phe Leu Phe Leu Asn Val Ser Gly Trp His Thr Tyr Phe Trp
305                 310                 315                 320

Ile Ala Phe Ile Pro Phe Val Leu Leu Ala Val Gly Thr Lys Leu
            325                 330                 335

Glu His Val Ile Thr Gln Leu Ala His Glu Val Ala Lys His Val
            340                 345                 350

Ala Ile Glu Gly Asp Leu Val Val Gln Pro Phe Asp Asp His Phe Trp
            355                 360                 365

Phe Gln Arg Pro Arg Ile Val Leu Phe Leu Ile His Phe Ile Leu Phe
            370                 375                 380

Gln Asn Ala Phe Glu Ile Gly Phe Phe Phe Trp Ile Trp Val Gln Tyr
385                 390                 395                 400

Gly Phe Asp Ser Cys Ile Met Gly Gln Val Arg Tyr Ile Ile Pro Arg
            405                 410                 415

Leu Ile Ile Gly Val Phe Val Gln Val Leu Cys Ser Tyr Ser Thr Leu
            420                 425                 430

Pro Leu Tyr Ala Ile Val Thr Gln Met Gly Ser Ser Phe Lys Lys Ala
            435                 440                 445

Ile Phe Asp Glu His Val Gln Val Gly Leu Val Gly Trp Ala Gln Lys
            450                 455                 460

Val Lys Lys Arg Lys Gly Leu Arg Ala Ala Ala Asp Gly Ser Ser Gln
465                 470                 475                 480

Gly Val Lys Glu Gly Gly Ser Thr Val Gly Ile Gln Leu Gly Asn Val
            485                 490                 495

Met Arg Lys Ala Ser Ala Pro Gln Glu Ile Lys Pro Asp Asp Ser Lys
            500                 505                 510

Ser Thr His
        515

<210> SEQ ID NO 9
<211> LENGTH: 1626
<212> TYPE: DNA
<213> ORGANISM: Cucumis melo

<400> SEQUENCE: 9
atgggtggcg gtggtggtgg cggtgctccg agtagggagt tagatcaaac tccgacatgg     60
gccgttgccg ctgtttgtgc agtcatcatt cttatttcca tcatattgga aaaggttctt    120
cacatggttg agagatatt tcagaaaagg aaaagaaag ccttgtatga agcccttgag     180
aaagttaaag gagagcttat ggtcttagga ttcatttctt tgctcttaac atttgggcaa    240

```
aattatattg ctaaagtttg catacoctca aagtatgaaa atactatgtt gccttgccct      300
tatagaggga gtactactgc acctaaaagc tcccatggtg gtgagcccga agatcatgat      360
gaagagacta cagatcacca tcgtaggctt ctttggtacg agcatcgaca tctagctggt      420
ggtggtcctg tagaaggttg caaaccaggg tatacacaac ttatatctct aaatggtctg      480
catcaaatac atattttcat cttctttcta gccgttctcc atgttgtatt tagcgccata      540
acgatgactc tcggaagatt gaaaattcgt ggatggaagg tatgggaaag acagaccgaa      600
caagaacatg atgccatgaa cgatcctaca aggtttagac ttactcatga gacatccttt      660
gtaagagacc atagcagttt ttggactaaa acacccctct ccttttacgt atccttctgg      720
aggcaattct ttaggtccgt tagtaggcca gattacttgt cccttagaca tggttttgtc      780
accgttcatt tagcccctgg gagtaaattt gactttcaga aatacatcaa aaggtcatta      840
gaagatgact ttaaggtggt cgtgggaatc acgagtcctc tgctatgggc atcaatggtg      900
cttttttctgc ttctcaatgt tagtgggtgg caagttatgt tttgggtgtc catatttcct      960
ctagtggtga tcttagccgt tggaacaaag ttgcaaggaa ttataacgca aatggctctt     1020
gaaatcaaag aaagacatgc agtggttcaa gggattcccc ttgttcaagt ctctgataga     1080
cacttttggt ttagttggcc cgttttggtt ctttatctca tccactatgt ccttttccag     1140
aatgcatttg agattacata tttcttttgg atatggtatg aatttgggtt gagatcgtgc     1200
tttcatgaca actttgatct tattatcgtg agagttgccc taggggttgg agtccagatt     1260
ttgtgcagtt acattacact cccattatat gctcttgtaa ctcagggatc aacaatgaag     1320
aaatccatat ttgatgaaca aacttcgaaa gcattgaagc aatggcatag aagtgctttg     1380
aagaaaaaga acgaaggagg aaagcctgaa tcaacgccga tgcgaacttt aggcggtgtc     1440
ggaggaagcc cccccgagtc accgatacaa ccttcgcatg atcagttcca acatcaatcg     1500
gtcaatcaat tatcatcacc aaccgacgtc gaagcctccg cccagcttcc ttcagccgac     1560
gtaatggcta ccgttgatct ccaccaccac caacaaaact atgctaatcg tgacttgttg     1620
agttga                                                               1626
```

<210> SEQ ID NO 10
<211> LENGTH: 541
<212> TYPE: PRT
<213> ORGANISM: Cucumis melo

<400> SEQUENCE: 10

```
Met Gly Gly Gly Gly Gly Gly Ala Pro Ser Arg Glu Leu Asp Gln
1               5                   10                  15

Thr Pro Thr Trp Ala Val Ala Val Cys Ala Val Ile Ile Leu Ile
            20                  25                  30

Ser Ile Ile Leu Glu Lys Val Leu His Met Val Gly Glu Ile Phe Gln
        35                  40                  45

Lys Arg Lys Lys Lys Ala Leu Tyr Glu Ala Leu Glu Val Lys Gly
    50                  55                  60

Glu Leu Met Val Leu Gly Phe Ile Ser Leu Leu Leu Thr Phe Gly Gln
65                  70                  75                  80

Asn Tyr Ile Ala Lys Val Cys Ile Pro Ser Lys Tyr Glu Asn Thr Met
                85                  90                  95

Leu Pro Cys Pro Tyr Arg Gly Ser Thr Thr Ala Pro Lys Ser Ser His
            100                 105                 110

Gly Gly Glu Pro Glu Asp His Asp Glu Glu Thr Thr Asp His His Arg
```

-continued

```
            115                 120                 125
Arg Leu Leu Trp Tyr Glu His Arg His Leu Ala Gly Gly Pro Val
130                 135                 140
Glu Gly Cys Lys Pro Gly Tyr Thr Gln Leu Ile Ser Leu Asn Gly Leu
145                 150                 155                 160
His Gln Ile His Ile Phe Ile Phe Phe Leu Ala Val Leu His Val Val
                165                 170                 175
Phe Ser Ala Ile Thr Met Thr Leu Gly Arg Leu Lys Ile Arg Gly Trp
                180                 185                 190
Lys Val Trp Glu Arg Gln Thr Glu Gln Glu His Asp Ala Met Asn Asp
                195                 200                 205
Pro Thr Arg Phe Arg Leu Thr His Glu Thr Ser Phe Val Arg Asp His
210                 215                 220
Ser Ser Phe Trp Thr Lys Thr Pro Leu Ser Phe Tyr Val Ser Phe Trp
225                 230                 235                 240
Arg Gln Phe Phe Arg Ser Val Ser Arg Pro Asp Tyr Leu Ser Leu Arg
                245                 250                 255
His Gly Phe Val Thr Val His Leu Ala Pro Gly Ser Lys Phe Asp Phe
                260                 265                 270
Gln Lys Tyr Ile Lys Arg Ser Leu Glu Asp Asp Phe Lys Val Val Val
                275                 280                 285
Gly Ile Thr Ser Pro Leu Leu Trp Ala Ser Met Val Leu Phe Leu Leu
290                 295                 300
Leu Asn Val Ser Gly Trp Gln Val Met Phe Trp Val Ser Ile Phe Pro
305                 310                 315                 320
Leu Val Val Ile Leu Ala Val Gly Thr Lys Leu Gln Gly Ile Ile Thr
                325                 330                 335
Gln Met Ala Leu Glu Ile Lys Glu Arg His Ala Val Val Gln Gly Ile
                340                 345                 350
Pro Leu Val Gln Val Ser Asp Arg His Phe Trp Phe Ser Trp Pro Val
                355                 360                 365
Leu Val Leu Tyr Leu Ile His Tyr Val Leu Phe Gln Asn Ala Phe Glu
370                 375                 380
Ile Thr Tyr Phe Phe Trp Ile Trp Tyr Glu Phe Gly Leu Arg Ser Cys
385                 390                 395                 400
Phe His Asp Asn Phe Asp Leu Ile Ile Val Arg Val Ala Leu Gly Val
                405                 410                 415
Gly Val Gln Ile Leu Cys Ser Tyr Ile Thr Leu Pro Leu Tyr Ala Leu
                420                 425                 430
Val Thr Gln Gly Ser Thr Met Lys Lys Ser Ile Phe Asp Glu Gln Thr
                435                 440                 445
Ser Lys Ala Leu Lys Gln Trp His Arg Ser Ala Leu Lys Lys Lys Asn
                450                 455                 460
Glu Gly Gly Lys Pro Glu Ser Thr Pro Met Arg Thr Leu Gly Gly Val
465                 470                 475                 480
Gly Gly Ser Pro Pro Glu Ser Pro Ile Gln Pro Ser His Asp Gln Phe
                485                 490                 495
Gln His Gln Ser Val Asn Gln Leu Ser Ser Pro Thr Asp Val Glu Ala
                500                 505                 510
Ser Ala Gln Leu Pro Ser Ala Asp Val Met Ala Thr Val Asp Leu His
                515                 520                 525
His His Gln Gln Asn Tyr Ala Asn Arg Asp Leu Leu Ser
530                 535                 540
```

<210> SEQ ID NO 11
<211> LENGTH: 1716
<212> TYPE: DNA
<213> ORGANISM: Cucumis melo

<400> SEQUENCE: 11

```
atgtctgttt tttgtctttg cttctgcctt ttatttactg gcgtcgccgc gtccggtgga      60
gacggcagcc cccactccag ggatctcgat aacacaccca cctgggctgt tgctgctgtt     120
tgcttctttt tcgtccttat ttccattgtc ttggaaaatg ttcttcacaa acttggaacg     180
tggttgacag aaaagcgcaa gagttctctg tatgaagctc tggagaaggt taaggctgag     240
ttgatgattt tgggtttcat ctccctgctt ctgacttttg ctcaagcata tatagtccaa     300
atctgtattc ctccgtccat tgcaaactcc atgttgccct gtccccttaa agagaaagat     360
gcctcatcat ctacaaccga tgaagacgaa catcaccgga gactacaatg ctaattcga     420
agatcattgg ctggaggtca caatgtcgtc tcgtgtaagg atggtaaggt gtctcttata     480
tctattgatg gattgcatca gttgcacatt ctcattttct tcttggccgt gtttcatgtg     540
ctctttagtg ttatcacaat gacacttgga agggtaaaga ttcgaggctg aaggagtgg     600
gagcaggaaa ctttaacgca taactatgag tttttcaatg atcctgcaag atttacgctt     660
actcacgaga catcttttgt gaaagcacac accagctttt ggacacgtct tcctttcttc     720
ttctatatta gttgcttctt caggcaattt tatgggtctg ttagtagggc tgattacttg     780
acgctgcgca acggattcat aacagtccat ttagcacctg gaagtaaatt taacttccag     840
agatatatca aaaggtcatt agaagatgac tttaaggtag tcgtcggtgt gagtcctttt     900
ctgtggtcga catttgtgat cttcctgatc tttaatcgat ctggatggca tacattgttc     960
tgggcatcat ttatccctct gcttataatc ttagcggttg atcaaaaact tcaagccatt    1020
ttgactagga tggctcttga aatctctgag aaacatgcag tggtccaggg aattccactc    1080
gtgcaaggat ccgacaagta tttctggttc ggtcgccctc aactgattct tcatctcatg    1140
cattttgctt tatttcagaa tgcattccag accacctata ttttgtctac actgtattct    1200
tttggcctga attcttgctt ctttggtggt cgcatcctta caattataaa agttggttta    1260
ggggtagtag cattatttct ttgcagctac gttacgcttc caatatacgc ccttgtaaat    1320
cagatgggtt caggtatgaa gaggtccatc tttgatgaac agacatcaaa ggcactcaag    1380
aaatggcacg aaacggccaa gaagaagcgg gctaaacgag cctcagcaac taaaaccctc    1440
ggaggtagtt caaatgcttc acctctacgc tcattgcgac ggttaaaaac tacaggacac    1500
tccatacgtg tgcctacgta tgaggacctt gagtcatctg attacgaggg cgatccatca    1560
gcaacaccta cacaagtgtc aacaagtgaa tcgattaatg ttgatgtaga agatggagat    1620
gaaatacaag aaatcgctga aacagagcaa tcccacagta caatgcaaag taagaagga    1680
gatgagttct catttataaa gcctgcacca ctagga                               1716
```

<210> SEQ ID NO 12
<211> LENGTH: 572
<212> TYPE: PRT
<213> ORGANISM: Cucumis melo

<400> SEQUENCE: 12

```
Met Ser Val Phe Cys Leu Cys Phe Cys Leu Leu Phe Thr Gly Val Ala
 1               5                  10                  15

Ala Ser Gly Gly Asp Gly Ser Pro His Ser Arg Asp Leu Asp Asn Thr
```

```
                    20                  25                  30
    Pro Thr Trp Ala Val Ala Val Cys Phe Phe Val Leu Ile Ser
                35                  40                  45
    Ile Val Leu Glu Asn Val Leu His Lys Leu Gly Thr Trp Leu Thr Glu
                50                  55                  60
    Lys Arg Lys Ser Ser Leu Tyr Glu Ala Leu Glu Lys Val Lys Ala Glu
    65                  70                  75                  80
    Leu Met Ile Leu Gly Phe Ile Ser Leu Leu Thr Phe Ala Gln Ala
                    85                  90                  95
    Tyr Ile Val Gln Ile Cys Ile Pro Pro Ser Ile Ala Asn Ser Met Leu
                    100                 105                 110
    Pro Cys Pro Leu Lys Glu Lys Asp Ala Ser Ser Thr Thr Asp Glu
                115                 120                 125
    Asp Glu His His Arg Arg Leu Gln Trp Leu Ile Arg Arg Ser Leu Ala
                130                 135                 140
    Gly Gly His Asn Val Val Ser Cys Lys Asp Gly Lys Val Ser Leu Ile
    145                 150                 155                 160
    Ser Ile Asp Gly Leu His Gln Leu His Ile Leu Ile Phe Phe Leu Ala
                    165                 170                 175
    Val Phe His Val Leu Phe Ser Val Ile Thr Met Thr Leu Gly Arg Val
                180                 185                 190
    Lys Ile Arg Gly Trp Lys Glu Trp Glu Gln Glu Thr Leu Thr His Asn
                195                 200                 205
    Tyr Glu Phe Phe Asn Asp Pro Ala Arg Phe Thr Leu Thr His Glu Thr
                210                 215                 220
    Ser Phe Val Lys Ala His Thr Ser Phe Trp Thr Arg Leu Pro Phe Phe
    225                 230                 235                 240
    Phe Tyr Ile Ser Cys Phe Phe Arg Gln Phe Tyr Gly Ser Val Ser Arg
                    245                 250                 255
    Ala Asp Tyr Leu Thr Leu Arg Asn Gly Phe Ile Thr Val His Leu Ala
                260                 265                 270
    Pro Gly Ser Lys Phe Asn Phe Gln Arg Tyr Ile Lys Arg Ser Leu Glu
                275                 280                 285
    Asp Asp Phe Lys Val Val Val Gly Val Ser Pro Phe Leu Trp Ser Thr
                290                 295                 300
    Phe Val Ile Phe Leu Ile Phe Asn Arg Ser Gly Trp His Thr Leu Phe
    305                 310                 315                 320
    Trp Ala Ser Phe Ile Pro Leu Leu Ile Ile Leu Ala Val Gly Ser Lys
                    325                 330                 335
    Leu Gln Ala Ile Leu Thr Arg Met Ala Leu Glu Ile Ser Glu Lys His
                340                 345                 350
    Ala Val Val Gln Gly Ile Pro Leu Val Gln Gly Ser Asp Lys Tyr Phe
                355                 360                 365
    Trp Phe Gly Arg Pro Gln Leu Ile Leu His Leu Met His Phe Ala Leu
                370                 375                 380
    Phe Gln Asn Ala Phe Gln Thr Thr Tyr Ile Leu Ser Thr Leu Tyr Ser
    385                 390                 395                 400
    Phe Gly Leu Asn Ser Cys Phe Phe Gly Arg Ile Leu Thr Ile Ile
                    405                 410                 415
    Lys Val Gly Leu Gly Val Val Ala Leu Phe Leu Cys Ser Tyr Val Thr
                420                 425                 430
    Leu Pro Ile Tyr Ala Leu Val Asn Gln Met Gly Ser Gly Met Lys Arg
                435                 440                 445
```

```
Ser Ile Phe Asp Glu Gln Thr Ser Lys Ala Leu Lys Lys Trp His Glu
    450                 455                 460
Thr Ala Lys Lys Lys Arg Ala Lys Arg Ala Ser Ala Thr Lys Thr Leu
465                 470                 475                 480
Gly Gly Ser Ser Asn Ala Ser Pro Leu Arg Ser Leu Arg Arg Phe Lys
                485                 490                 495
Thr Thr Gly His Ser Ile Arg Val Pro Thr Tyr Glu Asp Leu Glu Ser
            500                 505                 510
Ser Asp Tyr Glu Gly Asp Pro Ser Ala Thr Pro Thr Gln Val Ser Thr
        515                 520                 525
Ser Glu Ser Ile Asn Val Asp Val Glu Asp Gly Asp Glu Ile Gln Glu
    530                 535                 540
Ile Ala Glu Thr Glu Gln Ser His Ser Thr Met Gln Ser Lys Glu Gly
545                 550                 555                 560
Asp Glu Phe Ser Phe Ile Lys Pro Ala Pro Leu Gly
                565                 570

<210> SEQ ID NO 13
<211> LENGTH: 1560
<212> TYPE: DNA
<213> ORGANISM: Cucumis melo

<400> SEQUENCE: 13
atggcgagtt tggaacgaac ccctacatgg gcagtggcca ctgtctgttt tctattgatt      60
ctcatttcca tttccacaga atatttgctt cactttcttg tcttttttcag catcaaaaga     120 aggaaatccc tcaggcaagc tctcgacaat atcaaatccg aattgatgct tttgggattt     180
gtatcgctgt tattgacggt gagcgagaaa ggaattgcta catttgcat tcctaagagt      240 ttgaatcaca aatttctgcc ctgtcccact atcaacttca attccactta cttcttggaa     300
gaacccaagt gtgattcaca ggtaaatatg aggagatggc agtcttggga agcaaaaacc     360
agaactttag aatatcaatt tacaactgat ccaagaagat tcaatttgc tcgtcaaaca      420 tcctttggca agaggcatct caaattctgg agtgaccatc acattttttcg atggccggta    480 attaacccct ttttttttgt ttctgcctgt tttgttagac aattttacga atctgtctcc     540
gcagctgatt atctcactct tagacatggt ttcattacgg ctcatcttgg agaaggaacc     600
aactttgact ccaaaagta tataagaaga gctctagaca atgatttcag tgtggttgtg     660
ggaatcagga gttggtgggt tgggtgttt tctgtaatct tcatattctt cagtgcacat      720
tggcatgcag ggtttcacag ctatctatgg cttcccttta ttccattatt aatgcttttg     780
ttggttggga caaaattaca agggattatg acggagatgt gtttggagag caatgagaag     840
tctcatgtcg tacgaggaac tctgcttgtt aggcccagtg accattattt tggttgggc     900 cgtcccaaat tgcttctcta tttcatacac ttcattttct tccagaactc atttcaatta    960 gcgtttttt catgggcatg gctgaaattt gggctgagat cgtgcttttca agagagata    1020 gcagatttgg taataggagt ttctgtgggg gtgttggtgc agttcatttg tggttatgtt    1080
actctccctc tctatgcact tgtagctcag atggggagtt cgatgaagaa aacggtattc    1140
acggaggggg tggttgaagg cctgaggaaa tggcaaggaa gagcgaagaa aaaggttgct    1200
cgaaggcgaa gatcaggcca acatggctgc gactacaact tctcatcaca gtcgccgccg    1260
cgtacatcag ttgacgccgg cgttgactcg ccgccatctt tcagactgga ggcggcgccg    1320
cccatggcat cagtggatta ttataatggt cgtttacaag gggcgggtgc caataataac    1380
```

```
aaacaatata ataataacaa caccaccact tgttcggctg ctgtttcagt tagtggcgat   1440
gaggataaac taaaaggcaa aaaccaatc gaagaggagg cggatcacaa acccatctca   1500
ttggatgcct ttgattgggc taccaaaata caccgtaatt tttcaagaca tgcaatgtag   1560
```

<210> SEQ ID NO 14
<211> LENGTH: 519
<212> TYPE: PRT
<213> ORGANISM: Cucumis melo

<400> SEQUENCE: 14

```
Met Ala Ser Leu Glu Arg Thr Pro Thr Trp Ala Val Ala Thr Val Cys
1               5                   10                  15

Phe Leu Leu Ile Leu Ile Ser Ile Ser Thr Glu Tyr Leu Leu His Phe
            20                  25                  30

Leu Val Phe Phe Ser Ile Lys Arg Arg Lys Ser Leu Arg Gln Ala Leu
        35                  40                  45

Asp Asn Ile Lys Ser Glu Leu Met Leu Leu Gly Phe Val Ser Leu Leu
50                  55                  60

Leu Thr Val Ser Glu Lys Gly Ile Ala Asn Ile Cys Ile Pro Lys Ser
65                  70                  75                  80

Leu Asn His Lys Phe Leu Pro Cys Pro Thr Ile Asn Phe Asn Ser Thr
                85                  90                  95

Tyr Phe Leu Glu Glu Pro Lys Cys Asp Ser Gln Val Asn Met Arg Arg
            100                 105                 110

Trp Gln Ser Trp Glu Ala Lys Thr Arg Thr Leu Glu Tyr Gln Phe Thr
        115                 120                 125

Thr Asp Pro Arg Arg Phe Gln Phe Ala Arg Gln Thr Ser Phe Gly Lys
    130                 135                 140

Arg His Leu Lys Phe Trp Ser Asp His Ile Phe Arg Trp Pro Val
145                 150                 155                 160

Ile Asn Pro Phe Phe Val Ser Ala Cys Phe Val Arg Gln Phe Tyr
                165                 170                 175

Glu Ser Val Ser Ala Ala Asp Tyr Leu Thr Leu Arg His Gly Phe Ile
            180                 185                 190

Thr Ala His Leu Gly Glu Gly Thr Asn Phe Asp Phe Gln Lys Tyr Ile
        195                 200                 205

Arg Arg Ala Leu Asp Asn Asp Phe Ser Val Val Gly Ile Arg Ser
    210                 215                 220

Trp Trp Val Trp Val Phe Ser Val Ile Phe Ile Phe Ser Ala His
225                 230                 235                 240

Trp His Ala Gly Phe His Ser Tyr Leu Trp Leu Pro Phe Ile Pro Leu
                245                 250                 255

Leu Met Leu Leu Leu Val Gly Thr Lys Leu Gln Gly Ile Met Thr Glu
            260                 265                 270

Met Cys Leu Glu Ser Asn Glu Lys Ser His Val Val Arg Gly Thr Leu
        275                 280                 285

Leu Val Arg Pro Ser Asp His Tyr Phe Trp Leu Gly Arg Pro Lys Leu
    290                 295                 300

Leu Leu Tyr Phe Ile His Phe Phe Phe Gln Asn Ser Phe Gln Leu
305                 310                 315                 320

Ala Phe Phe Ser Trp Ala Trp Leu Lys Phe Gly Leu Arg Ser Cys Phe
                325                 330                 335

Gln Arg Glu Ile Ala Asp Leu Val Ile Gly Val Ser Val Gly Val Leu
            340                 345                 350
```

Val Gln Phe Ile Cys Gly Tyr Val Thr Leu Pro Leu Tyr Ala Leu Val
        355                 360                 365

Ala Gln Met Gly Ser Ser Met Lys Lys Thr Val Phe Thr Glu Gly Val
        370                 375                 380

Val Glu Gly Leu Arg Lys Trp Gln Gly Arg Ala Lys Lys Lys Val Ala
385                 390                 395                 400

Arg Arg Arg Arg Ser Gly Gln His Gly Cys Asp Tyr Asn Phe Ser Ser
                405                 410                 415

Gln Ser Pro Pro Arg Thr Ser Val Asp Ala Gly Val Asp Ser Pro Pro
                420                 425                 430

Ser Phe Arg Leu Glu Ala Ala Pro Pro Met Ala Ser Val Asp Tyr Tyr
        435                 440                 445

Asn Gly Arg Leu Gln Gly Ala Gly Ala Asn Asn Lys Gln Tyr Asn
        450                 455                 460

Asn Asn Asn Thr Thr Thr Cys Ser Ala Ala Val Ser Val Ser Gly Asp
465                 470                 475                 480

Glu Asp Lys Leu Lys Gly Lys Lys Pro Ile Glu Glu Ala Asp His
                485                 490                 495

Lys Pro Ile Ser Leu Asp Ala Phe Asp Trp Ala Thr Lys Ile His Arg
        500                 505                 510

Asn Phe Ser Arg His Ala Met
        515

<210> SEQ ID NO 15
<211> LENGTH: 23
<212> TYPE: DNA
<213> ORGANISM: Artificial Sequence
<220> FEATURE:
<223> OTHER INFORMATION: Mlo2-5 Primer pair WT gene 1

<400> SEQUENCE: 15
acgtggaagt cgtgggagga aga                                         23

<210> SEQ ID NO 16
<211> LENGTH: 23
<212> TYPE: DNA
<213> ORGANISM: Artificial Sequence
<220> FEATURE:
<223> OTHER INFORMATION: Mlo2-5 Primer pair WT gene 2

<400> SEQUENCE: 16
attcgttacc gggagcaaaa tgc                                         23

<210> SEQ ID NO 17
<211> LENGTH: 22
<212> TYPE: DNA
<213> ORGANISM: Artificial Sequence
<220> FEATURE:
<223> OTHER INFORMATION: Mlo2-5 Primer pair mutated gene 1

<400> SEQUENCE: 17
ttcataacca atctcgatac ac                                          22

<210> SEQ ID NO 18
<211> LENGTH: 23
<212> TYPE: DNA
<213> ORGANISM: Artificial Sequence
<220> FEATURE:
<223> OTHER INFORMATION: Mlo2-5 Primer pair mutated gene 2

<400> SEQUENCE: 18

```
acgtggaagt cgtgggagga aga                                          23

<210> SEQ ID NO 19
<211> LENGTH: 22
<212> TYPE: DNA
<213> ORGANISM: Artificial Sequence
<220> FEATURE:
<223> OTHER INFORMATION: Mlo6-2 Primer pair mutated gene 1

<400> SEQUENCE: 19
ttcataacca atctcgatac ac                                           22

<210> SEQ ID NO 20
<211> LENGTH: 23
<212> TYPE: DNA
<213> ORGANISM: Artificial Sequence
<220> FEATURE:
<223> OTHER INFORMATION: Mlo6-2 Primer pair mutated gene 2

<400> SEQUENCE: 20
acaagaactg gtttcattta gca                                          23

<210> SEQ ID NO 21
<211> LENGTH: 27
<212> TYPE: DNA
<213> ORGANISM: Artificial Sequence
<220> FEATURE:
<223> OTHER INFORMATION: Mlo12-1 Primer pair WT gene 1

<400> SEQUENCE: 21
tggagcaagt ctacctttac cctctgg                                      27

<210> SEQ ID NO 22
<211> LENGTH: 23
<212> TYPE: DNA
<213> ORGANISM: Artificial Sequence
<220> FEATURE:
<223> OTHER INFORMATION: Mlo12-1 Primer pair WT gene 2

<400> SEQUENCE: 22
tcagtgggct gcattcacac aaa                                          23

<210> SEQ ID NO 23
<211> LENGTH: 28
<212> TYPE: DNA
<213> ORGANISM: Artificial Sequence
<220> FEATURE:
<223> OTHER INFORMATION: Mlo12-1 Primer pair mutated gene 1

<400> SEQUENCE: 23
ggtgcagcaa aacccacact tttacttc                                     28

<210> SEQ ID NO 24
<211> LENGTH: 27
<212> TYPE: DNA
<213> ORGANISM: Artificial Sequence
<220> FEATURE:
<223> OTHER INFORMATION: Mlo12-1 Primer pair mutated gene 2

<400> SEQUENCE: 24
tggagcaagt ctacctttac cctctgg                                      27
```

POWDERY MILDEW RESISTANCE PROVIDING GENES IN *CUCUMIS MELO*

CROSS-REFERENCE TO RELATED APPLICATIONS

This application is a divisional application of U.S. patent application Ser. No. 14/002,259, filed Aug. 29, 2013, which is the United States national phase of International Application No. PCT/EP2012/053208 filed Feb. 24, 2012, and claims priority to International Application No. PCT/EP2011/053053, filed Mar. 1, 2011, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1704760_ST25.txt. The size of the text file is 57,737 bytes, and the text file was created on May 22, 2017.

BACKGROUND OF THE INVENTION

Field of the Invention

The present invention relates to powdery mildew resistance providing genes of *Cucumis melo*, wherein said resistance is provided by impairment of the present genes either at the expression or protein level. Further, the present invention relates to plants comprising the present resistance conferring genes and seeds, embryos or other propagation material thereof.

Powdery mildew (PM) is one of the main fungal diseases known in plants belonging to the *Cucumis* family such as *Cucumis melo* (melon), both in the field and greenhouse.

Powdery mildew diseases are generally caused by many different species of fungi of the order Erysiphales. The disease is characterized by distinctive symptoms such as white powder-like spots on the leaves and stems. Generally, the lower leaves are the most affected, but the mildew can appear on any part of the plant that is exposed above ground. As the disease progresses, the spots get larger and thicker as massive numbers of spores form, and the mildew spreads up and down the length of the plant such on the stem and even the fruits.

Severely affected leaves can become dry and brittle, or can wither and die. Because of the infection, the fruits can be smaller in size, fewer in number, less able to be successfully stored, sun scalded, incompletely ripe, and having a poor flavor. It may also predispose plants to be more vulnerable to other pathogens. Eventually, the plant can die.

Powdery mildew can, amongst others, be caused by the fungus *Sphaerotheca fuliginea* (recently renamed: *Podosphaera xanthii* also designated as *Oidium erysiphoides*) and/or *Erysiphe cichoracearum* DC (recently renamed: *Golovinomyces cichoracearum* also designated as *Oidium chrysanthemi*).

Considering the economic importance of *Cucumis* plant species, such as melon, there is a continued need in the art to provide powdery mildew resistance providing genes.

In view of the above need in the art, it is an object of the present invention, amongst other objects, to meet this need.

SUMMARY OF THE INVENTION

According to the present invention, this object, amongst other objects, is met by an powdery mildew resistance conferring gene as defined in the appended claim 1.

Specifically, this object of the present invention, amongst other objects, is met by a powdery mildew resistance conferring gene, wherein the amino acid sequence encoded by said resistance conferring gene is selected from the group consisting of SEQ ID No. 2, SEQ ID No. 4, SEQ ID No. 6, SEQ ID No. 8, SEQ ID No. 10, SEQ ID No. 12 and SEQ ID No. 14, and amino acid sequences with more than 70% identity, preferably more than 80% identity, more preferably more than 90% identity, and most preferably more than 95% identity such as more than 96%, 97%, 98%, 99%; and wherein said resistance conferring gene is impaired.

The object of the present invention, amongst other objects, is additionally met by a powdery mildew resistance conferring gene, wherein the cDNA sequence transcribed from said resistance conferring gene is selected from the group consisting of SEQ ID No. 1, SEQ ID No. 3, SEQ ID No. 5, SEQ ID No. 7, SEQ ID No. 9, SEQ ID No. 11 and SEQ ID No. 13, and cDNA sequences with more than 70% identity, preferably more than 80% identity, more preferably more than 90% identity, and most preferably more than 95% identity such as more than 96%, 97%, 98%, 99%; and wherein said resistance conferring gene is impaired.

DESCRIPTION OF THE INVENTION

Figure 1:
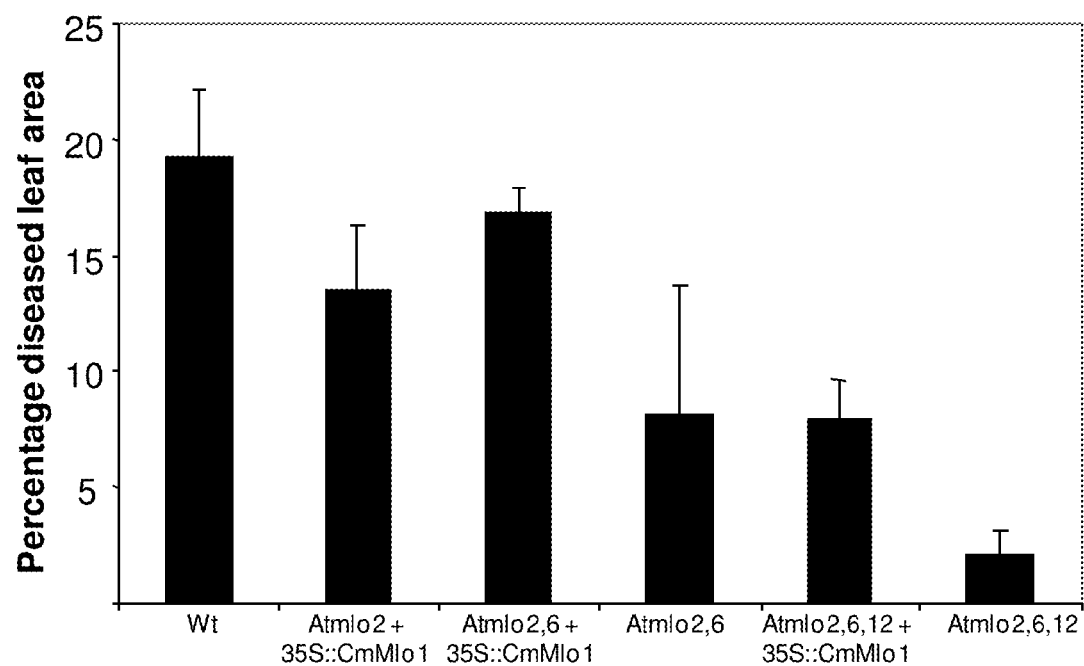
FIG. 1: shows the results of the complementation assay for 35S::CmKIP1_cDNA (designated 35S::CmMlo1_cDNA) which resulted in a gain-of-function for the powdery mildew susceptibility pathway. The percentage of diseased leaf area 12 days post inoculation is shown for *Arabidopsis* WT, Atmlo2/6 and Atmlo2/6/12 mutants, the data represent mean±s.d. of 2 individuals. For Atmlo2+35S::CmKIP1_cDNA, Atmlo2/6+35S::CmKIP1_cDNA and Atmlo2/6/12+35S::CmKIP1_cDNA the data represent mean±s.d. of respectively 4, 4 and 9 primary transformants.

Impaired resistance conferring gene according to the present invention is meant to indicate a gene providing a reduced, or even absent, susceptibility to powdery mildew caused by fungi indicated by powder-like spots on the leaves and stems, such as fungi belonging to the order Erysiphales such as *Sphaerotheca fuliginea* (recently renamed:

*Podosphaera xanthii* also designated as *Oidium erysiphoides*) and/or *Erysiphe cichoracearum* DC.

Impaired resistance conferring gene according to the present invention are mutated genes. The mutation of the present genes can through different mechanisms results in impairment. For example, mutations in protein encoding DNA sequences may lead to mutated, truncated or non-functional proteins. Mutations in non-coding DNA sequences may cause alternative splicing, translation or protein trafficking. Alternatively, a mutation resulting in an altered transcriptional activity of a gene, which determines the amount of mRNA available for translation to protein, may results in low levels, or absence, of proteins. Additionally, the impairment of gene function may be caused after translation, i.e. at protein level.

Impairment according to the present invention is also indicated by observing a powdery mildew resistance in a *Cucumis melo* plant comprising a gene which as mutated at the protein level as compared to the SEQ ID Nos. provided herein or no expression of the SEQ ID Nos. provided herein is observed.

Impaired is also indicated herein as a non-functional gene or protein. Although the function of the present genes is not yet identified, a non-functional gene or protein can be readily determined by establishing powdery mildew resistance (non-functional) or powdery mildew susceptibility (functional) in a plant. A powdery mildew resistance (non-functional) plant is indicated by comprising a gene which as mutated at the protein level as compared to the SEQ ID Nos. provided herein or no expression of the SEQ ID Nos. provided herein is observed.

Functional and non-functional genes or proteins can also be determined using complementation experiments. For example, transforming a resistant powdery mildew *Cucumis melo* plant with any of the present genes or proteins will result in a powdery mildew susceptible *Cucumis melo* plant when the gene or protein is functional while the *Cucumis melo* plant will remain resistant when the gene or protein is non-functional.

According to the present invention, the present powdery mildew resistance conferring genes provide powdery mildew resistance when the present genes are impaired. Impaired according to the present invention can be indicated by the absence, or decrease of a functional, or non-muted, protein identified herein as SEQ ID No. 2, SEQ ID No. 4, SEQ ID No. 6, SEQ ID No. 8, SEQ ID No. 10, SEQ ID No. 12 or SEQ ID No. 14. In the art, many mechanisms are known resulting in the impairment of a gene either at the transcription, translation or protein level.

For example, impairment at the transcription level can be the result of one or more mutations in transcription regulation sequences, such as promoters, enhancers, and initiation, termination or intron splicing sequences. These sequences are generally located 5' of, 3' of, or within the coding sequence represented by SEQ ID No. 1, SEQ ID No. 3, SEQ ID No. 5, SEQ ID No. 7, SEQ ID No. 9, SEQ ID No. 11 or SEQ ID No. 13. Impairment can also be provided by a deletion, rearrangement or insertion in the present genes.

Impairment at the translation level can be provided by a premature stop-codons or other RNA→protein controlling mechanisms (such as splicing) or posttranslational modifications influencing, for example, protein folding or cellular trafficking.

Impairment at the protein level can be provided by truncated, misfolded or disturbed protein-protein interactions.

Independent of the underlying mechanism, impairment according to the present invention is indicated by an decrease or absence a functional protein according to SEQ ID No. 2, SEQ ID No. 4, SEQ ID No. 6, SEQ ID No. 8, SEQ ID No. 10, SEQ ID No. 12 or SEQ ID No. 14.

According to a preferred embodiment, impairment according to the present invention is provided by one or more mutations in the present genes resulting in the absence of a protein expression product. As indicated, these mutations can cause a defective expression at the transcription or translation level.

According to another preferred embodiment, impairment according to the present invention is caused by one or more mutations in the present genes resulting in a non-functional protein expression product. A non-functional protein expression product can, for example, be caused by premature stop-codons, incorrect translation or posttranslational processing or by insertions, deletions or amino acid changes.

Using molecular biology methods, impairment of the present genes can also be accomplished by gene silencing, for example using siRNA or knocking out of the present genes. Methods based on EMS or other mutagenic chemical compounds capable of randomly change nucleic acids into other nucleotides are also contemplated within the context of the present invention. Detection of such mutations typically involves high sensitivity melting curve analyses or nucleotide sequencing-based TILLING procedures.

The present invention relates to nucleotide and amino acid sequences with more than 70%, preferably more than 80%, more preferably more than 90% and most preferably more than 95% sequence identity either at the nucleotide level or the amino acid level.

Sequence identity as used herein is defined as the number of identical consecutive aligned nucleotides, or amino acids, over the full length of the present sequences divided by the number of nucleotides, or amino acids, of the full length of the present sequences and multiplied by 100%. For example, a sequence with 80% identity to SEQ ID No. 1 comprises over the total length of 1713 nucleotides of SEQ ID No. 1 1370 or 1371 identical aligned consecutive nucleotides, i.e., 1370 or 1371/1713*100%=80%.

According to the invention, the present genes are derived from *Cucumis melo*.

According to another aspect, the present invention relates to *Cucumis melo* plants comprising in their genome the present impaired powdery mildew resistance conferring genes, i.e., plants not expressing a functional protein selected from the group consisting of SEQ ID No. 2, SEQ ID No. 4, SEQ ID No. 6, SEQ ID No. 8, SEQ ID No. 10, SEQ ID No. 12 and SEQ ID No. 14, and amino acid sequences with more than 70% identity, preferably more than 80% identity, more preferably more than 90% identity, and most preferably more than 95% identity.

In general, and preferably, the present plants will be homozygous for the present impaired genes, i.e., comprising two impaired powdery mildew resistance conferring genes, wherein the cDNA sequence transcribed from said resistance conferring gene is selected from the group consisting of SEQ ID No. 1, SEQ ID No. 3, SEQ ID No. 5, SEQ ID No.

7, SEQ ID No. 9, SEQ ID No. 11 and SEQ ID No. 13, and cDNA sequences with more than 70% identity, preferably more than 80% identity, more preferably more than 90% identity, and most preferably more than 95% identity.

Considering the benefits of the present plants, i.e., providing powdery mildew resistance in melon plants, the invention also relates to seeds, plant parts or propagation material capable of providing the present powdery mildew resistant melon plants which seeds, plant parts or propagation material comprise one or more of the present powdery mildew resistance conferring genes, i.e., impaired powdery mildew resistance conferring genes, wherein the cDNA sequence transcribed from said resistance conferring gene is selected from the group consisting of SEQ ID No. 1, SEQ ID No. 3, SEQ ID No. 5, SEQ ID No. 7, SEQ ID No. 9, SEQ ID No. 11 and SEQ ID No. 13, and cDNA sequences with more than 70% identity, preferably more than 80% identity, more preferably more than 90% identity, and most preferably more than 95% identity.

According to yet another aspect, the present invention relates to isolated nucleotide sequences selected from the group consisting of SEQ ID No. 1, SEQ ID No. 3, SEQ ID No. 5, SEQ ID No. 7, SEQ ID No. 9, SEQ ID No. 11 and SEQ ID No. 13, and nucleotide sequences with more than 70% identity, preferably more than 80% identity, more preferably more than 90% identity, and most preferably more than 95% identity.

According to still another aspect, the present invention relates to isolated amino acid sequences selected from the group consisting of SEQ ID No. 2, SEQ ID No. 4, SEQ ID No. 6, SEQ ID No. 8, SEQ ID No. 10, SEQ ID No. 12 and SEQ ID No. 14, and amino acid sequences with more than 70% identity, preferably more than 80% identity, more preferably more than 90% identity, and most preferably more than 95% identity.

The present invention also relates to the use of one or more of the present powdery mildew resistance conferring genes, one or more of the present isolated nucleotide sequences, or one or more of the present isolated amino acid sequences for providing a powdery mildew resistant melon plants (*Cucumis melo*). As indicated, the present use is based on impairment, either at the expression or protein level, of the genes described herein and can be readily determined by the presently provided cDNA and amino acid sequences optionally in combination with determination of the presence or absence of powdery mildew resistance and/or in combination with complementation assays.

The present invention will be further described in the examples below of preferred embodiments of the present invention. In the example, reference is made to figures wherein:

EXAMPLES

Example 1 Complementation of *Arabidopsis Thaliana* Atmlo Mutant Plants

Material and Methods

Full length cDNA of melon CmKIP genes were cloned either in pBINPLUS or Gateway vectors under control of a 35S promoter using standard cloning techniques.

In order to analyze the in planta function of identified melon powdery mildew resistance genes, via the Nottingham *Arabidopsis* Stock Centre (University of Nottingham, Sutton Bonington Campus, Loughborough, LE12 5RD, United Kingdom), seeds were obtained of *Arabidopsis thaliana* ecotype Columbia (Col) mutant line NACS ID N9707 (mlo2-5 single mutant), N9710 (mlo2-5, mlo6-2 double mutant) and N9715 (mlo2-5, mlo6-2, mlo12-1 triple mutant).

The seeds were cultivated in soil, DNA was extracted and PCR assays with primers flanking the mutations (Table 1) were used to screen 4-week-old plants for the presence of the mutations as described at The *Arabidopsis* Information Resource (TAIR).

TABLE 1

Primer pairs used to identify WT gene versus mutated Mlo homologue in *Arabidopsis* mutant lines (5' to 3').

| | Primer pair WT gene | | Primer pair mutated gene | |
|---|---|---|---|---|
| Mlo2-5 | acgtggaagtcgtggg aggaaga (SEQ ID NO: 15) | attcgttaccgggagc aaaatgc (SEQ ID NO: 16) | ttcataaccaatctcgat acac (SEQ ID NO: 17) | acgtggaagtcgtggg aggaaga (SEQ ID NO: 18) |
| Mlo6-2 | | | ttcataaccaatctcgat acac (SEQ ID NO: 19) | acaagaactggtttcat ttagca (SEQ ID NO: 20) |
| Mlo12-1 | tggagcaagtctacctt taccctctgg (SEQ ID NO: 21) | tcagtgggctgcattca cacaaa (SEQ ID NO: 22) | ggtgcagcaaaaccc acactttacttc (SEQ ID NO: 23) | tggagcaagtctacctt taccctctgg (SEQ ID NO: 24) |

The floral dip method was used to transform *Arabidopsis thaliana* ecotype Columbia and the single, double and triple mutants with constructs harboring the putative melon Mlo orthologs. After selection of the transformant plants on kanamycin, analyses were performed to identify the resistant versus susceptible phenotypes upon powdery mildew (*Golovinomyces orontii*) infection.

Dr. R. Panstruga (MPI, Cologne, Germany) kindly provided *Arabidopsis thaliana* ecotype Columbia leaves infected with *Golovinomyces orontii*. To maintain a fresh growing *Golovinomyces orontii* culture, leaves with sporulating *Golovinomyces orontii* were used every 10-14 days to rub-infect fresh *Arabidopsis thaliana* ecotype Columbia leaves. In addition, the mlo single, double and triple mutants and their progeny, complemented with the melon Mlo candidate genes, were inoculated with sporulating *Golovinomyces orontii* in order to confirm the powdery mildew susceptibility levels.

Results

To confirm the predicted involvement of the identified CmKIP genes in susceptibility to powdery mildew, full length cDNA sequences of CmKIP1, CmKIP2, CmKIP3 and CmKIP4 were expressed in *Arabidopsis* using the ubiquitous 35S promoter. In addition, also a full length genomic fragment was expressed for CmKIP2 using the 35S promoter.

The 35S::CmKIP1_cDNA, 35S::CmKIP2_cDNA, 35S::CmKIP2_genomic, 35S::CmKIP3_cDNA and 35S::CmKIP4_cDNA constructs were transformed to *Arabidopsis* mutant line NACS ID N9707 (mlo2-5 single mutant), N9710 (mlo2-5, mlo6-2 double mutant) and N9715 (mlo2-5, mlo6-2, mlo12-1 triple mutant). In addition, to examine epistatic effects of CmKIP overexpression in *Arabidopsis*, also WT Columbia plants were transformed with the same series of constructs.

Figure 2:
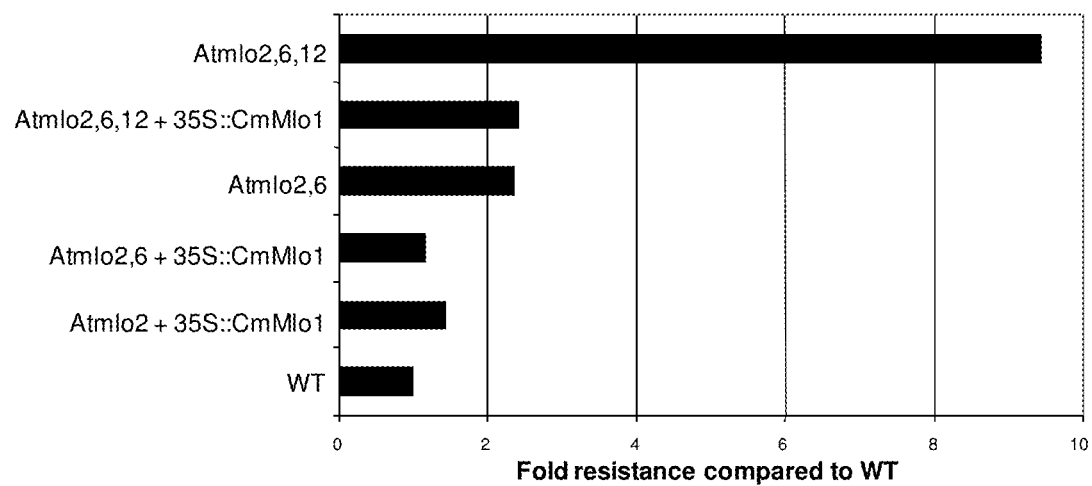
FIG. 2: shows the results of the complementation assay for 35S::CmKIP1_cDNA (designated 35S::CmMlo1_cDNA) which resulted in a gain-of-function for the powdery mildew susceptibility pathway. The level of resistance observed for Atmlo2/6 and Atmlo2/6/12 mutants and for primary transformants Atmlo2+35S::35S::CmKIP1_cDNA, Atmlo2/6+35S::35S::CmKIP1_cDNA and Atmlo2/6/12+35S::35S::CmKIP1_cDNA is presented in comparison to the *Arabidopsis* WT phenotype.

FIG. 1 and FIG. 2 show the results obtained for the complementation assay for the 35S::KIP1_cDNA construct. The *Arabidopsis* mutant Atmlo2 shows reduced susceptibility compared to WT Columbia (Col-0) (data not shown). The double mutant Atmlo2/6 is even more reduced in susceptibility to *Golovinomyces orontii*. The triple mutant Atmlo2/6/12 is fully resistant to *Golovinomyces orontii* infection.

Primary transformants of Atmlo2/6/12 with the 35S::CmKIP1_cDNA constructs retained susceptibility to *Golovinomyces orontii* infection to the levels of susceptibility compared to the Atmlo2/6 double mutant. Complementation of the Atmlo2/6 double mutant of *Arabidopsis* with the 35S::CmKIP1 construct resulted in plants with near WT levels of infection with *Golovinomyces orontii*.

A quick and strong development of the fungus resulting in sporulating hyphae was detected. Complementation of the Atmlo2/6/12 triple mutant of *Arabidopsis* with the 35S::CmKIP1_cDNA construct resulted in clear visible powdery mildew infections on inoculated leaves for most of the primary transformants analyzed. The retaining of susceptibility to *Golovinomyces orontii* of the *Arabidopsis* triple mutant previously shown to be full resistant to *Golovinomyces orontii* indicates that the identified CmKIP1 gene is able to reestablish the powdery mildew susceptibility pathway in *Arabidopsis*. With this result we showed we were able to identify CmKIP1, a gene functional in the powdery mildew susceptibility pathway.

Figure 3:
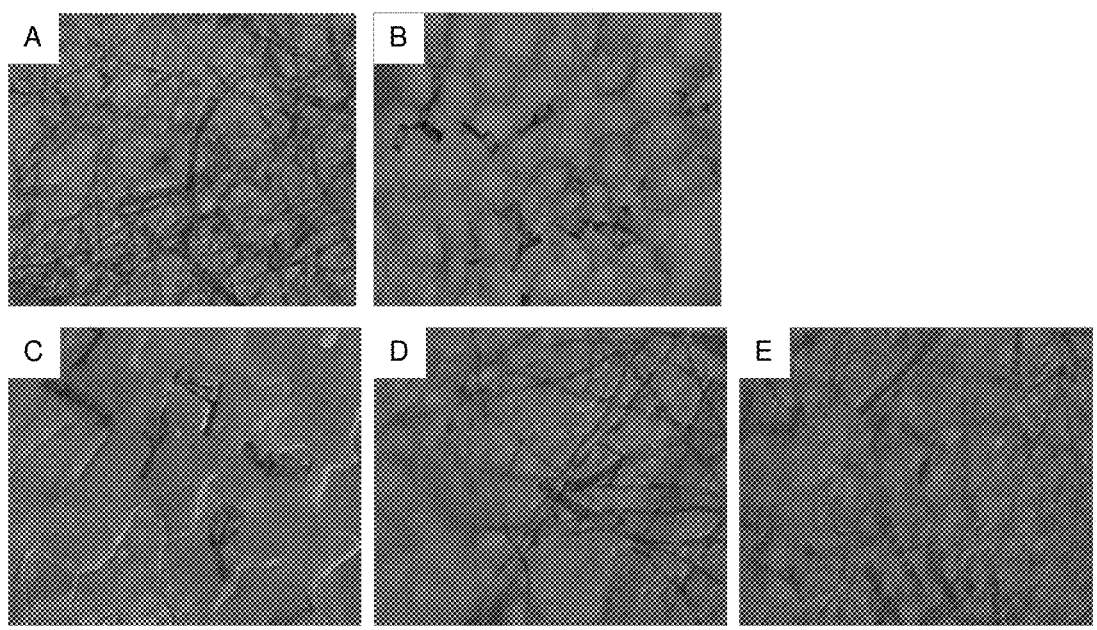
FIG. 3: shows complementation of Atmlo2/6/12 with the 35S::CmKIP2_cDNA which results in gain-of-function for the powdery mildew susceptibility pathway. (A) Susceptible interaction phenotype of *G. orontii* on leaves of WT Columbia; clear hyphae and conidiophore development. (B) Resistant interaction phenotype of *G. orontii* on leaves of Atmlo2/6/12; spores on the leaf surface have germinated but no further development is observed. (C, D, E) Intermediate interaction phenotypes observed on Atmlo2/6/12 after complementation with 35S::CmKIP2_cDNA; on some primary transformants the germinated spores do not further develop (C), on other primary transformants germination of spores is observed, hyphae do develop and conidiophores are formed (D,E).

FIG. 3 shows the results obtained for the complementation assay for the 35S::CmKIP2_cDNA construct. Primary transformants of Atmlo2/6/12 with the 35S::CmKIP2 cDNA constructs do in a few cases retain minor susceptibility symptoms to *Golovinomyces orontii* infection. However, this susceptibility is difficult to detect by eye and not all primary transformants show this weak susceptibility phenotype. To study in more detail the development of *Golovinomyces orontii*, microscopic studies were performed.

Leaves were washed for 48 hours in 70% EtOH and stained with CBB. With this microscopic screening a clear difference was observed between the powdery mildew resistant AtMlo2/6/12 mutant line and this line complemented with 35S::CmKIP2_cDNA.

Of the analyzed complemented lines, several showed clear development of hyphea in the leaves while all germinating spores on the triple mutant are stopped immediately after penetration in the leaves. On the 35S::CmKIP2_cDNA complemented lines the clear development of hyphae was detected which indicate that the CmKIP2 gene is able to reestablish the powdery mildew susceptibility pathway in *Arabidopsis*.

Comparable results, i.e. complementation in *Arabidopsis*, was observed, for the CmKIP3 overexpression contruct.

TABLE 2 cDNA and amino acid sequences

| powdery mildew gene identity | Plant | Sequence type | SEQ ID No. |
|---|---|---|---|
| CmKIP1 | *Cucumis melo* | cDNA | 1 |
|  |  | aa | 2 |
| CmKIP2 | *Cucumis melo* | cDNA | 3 |
|  |  | aa | 4 |
| CmKIP3 | *Cucumis melo* | cDNA | 5 |
|  |  | aa | 6 |
| CmKIP4 | *Cucumis melo* | cDNA | 7 |
|  |  | aa | 8 |
| CmKIP6 | *Cucumis melo* | cDNA | 9 |
|  |  | aa | 10 |
| CmKIP7 | *Cucumis melo* | cDNA | 11 |
|  |  | aa | 12 |
| CmKIP9 | *Cucumis melo* | cDNA | 13 |
|  |  | aa | 14 |

The invention claimed is:

1. A full length cDNA transcribed from a nucleotide sequence having the sequence of SEQ ID NO: 3.

2. A method for obtaining a melon plant that is resistant to powdery mildew, comprising introducing one or more mutations to a nucleotide sequence having the sequence of SEQ ID NO: 3 in a melon plant that is susceptible to powdery mildew, wherein the mutation results in a decrease, absence, or loss of function of a protein having the amino acid sequence of SEQ ID NO: 4 and resistance to powdery mildew.

3. The method according to claim 2, wherein the one or more mutations cause the absence of a protein.

4. The method according to claim 2, wherein the one or more mutations cause a non-functioning protein.

5. The method according to claim 2, wherein the one or more mutations cause gene silencing.

6. The method according to claim 2, wherein the one or more mutations are at least three mutations.

7. The method according to claim 2, wherein the resistance is to powdery mildew caused by *Golovinomyces orontii*.

* * * * *